United States Patent
Saura et al.

(10) Patent No.: US 11,311,842 B2
(45) Date of Patent: Apr. 26, 2022

(54) MEMBRANE SEPARATION DEVICE HAVING IMPROVED FILTRATION VELOCITY

(71) Applicant: Fenwal, Inc., Lake Zurich, IL (US)

(72) Inventors: Adrian G. Saura, Grayslake, IL (US); Carlos Calderon, Waukegan, IL (US)

(73) Assignee: Fenwal, Inc., Lake Zurich, IL (US)

( * ) Notice: Subject to any disclaimer, the term of this patent is extended or adjusted under 35 U.S.C. 154(b) by 22 days.

(21) Appl. No.: 15/376,349

(22) Filed: Dec. 12, 2016

(65) Prior Publication Data

US 2017/0182464 A1 Jun. 29, 2017

Related U.S. Application Data

(60) Provisional application No. 62/271,480, filed on Dec. 28, 2015.

(51) Int. Cl.
| | |
|---|---|
| *B01D 63/16* | (2006.01) |
| *A61M 1/34* | (2006.01) |
| *A61M 1/26* | (2006.01) |
| *B01D 69/10* | (2006.01) |
| *A61M 1/02* | (2006.01) |
| *B01D 63/06* | (2006.01) |

(Continued)

(52) U.S. Cl.
CPC ........... *B01D 63/16* (2013.01); *A61M 1/0218* (2014.02); *A61M 1/265* (2014.02); *A61M 1/3496* (2013.01); *B01D 63/063* (2013.01); *B01D 69/10* (2013.01); *B01D 71/48* (2013.01); *B01D 71/50* (2013.01); *B01D 71/56* (2013.01); *B01D 71/68* (2013.01); *B01D 2315/02* (2013.01)

(58) Field of Classification Search
CPC combination set(s) only.
See application file for complete search history.

(56) References Cited

U.S. PATENT DOCUMENTS

| | | | |
|---|---|---|---|
| 4,446,021 A * | 5/1984 | Aufderhaar | ........... B07B 1/4609 |
| | | | 210/378 |
| 5,053,121 A | 10/1991 | Schoendorfer et al. | |
| | (Continued) | | |

FOREIGN PATENT DOCUMENTS

| | | |
|---|---|---|
| WO | 2001005492 A1 | 1/2001 |
| WO | 2015167487 A1 | 11/2015 |

OTHER PUBLICATIONS

Partial European search report for application No. 16204452.3, dated May 8, 2017, 11 pages.

(Continued)

*Primary Examiner* — Bobby Ramdhanie
*Assistant Examiner* — Donovan Bui-Huynh
(74) *Attorney, Agent, or Firm* — Cook Alex Ltd.

(57) ABSTRACT

A blood filtration device comprising a generally cylindrical housing having an interior wall. An interior member is mounted interior of the housing and comprises an outer surface having a porous membrane disposed thereon. The housing and interior member are relatively rotatable and define an annular gap therebetween. The blood filtration device also comprises an inlet for directing fluid into the annular gap, a first outlet for exiting filtrate passing through the membrane, and a second outlet for directing from the annular gap the remaining retentate. The porous membrane comprises a first layer and a second layer.

16 Claims, 11 Drawing Sheets

(51) Int. Cl.
   *B01D 71/48*    (2006.01)
   *B01D 71/50*    (2006.01)
   *B01D 71/56*    (2006.01)
   *B01D 71/68*    (2006.01)

(56) References Cited

U.S. PATENT DOCUMENTS

| | | | |
|---|---|---|---|
| 5,194,145 | A | 3/1993 | Schoendorfer |
| 6,045,701 | A | 4/2000 | Ung-Chhun et al. |
| 6,416,665 | B1 | 7/2002 | Mcgrath |
| 7,784,619 | B2 | 8/2010 | Jacobson |
| 2003/0036085 | A1 | 2/2003 | Salinaro et al. |
| 2005/0144916 | A1* | 7/2005 | Adamek .............. B01D 29/213  55/484 |
| 2005/0274672 | A1* | 12/2005 | Tu ....................... A61M 1/3496  210/645 |
| 2010/0163488 | A1* | 7/2010 | Fislage ................. B01D 69/02  210/490 |
| 2014/0010738 | A1* | 1/2014 | Boggs ................. A61M 1/0272  422/534 |
| 2014/0072954 | A1* | 3/2014 | Umeda ................ C12N 5/0087  435/2 |
| 2015/0306539 | A1 | 10/2015 | Yamato |

OTHER PUBLICATIONS

G. Beaudoin, M. Y. Jaffrin. Plasma filtration in Couette flow membrane devices. Artif Organs. Feb. 1989;13(1):43-51.

Communication pursuant to Article 94(3) EPC for application No. 16204452.3, dated Jul. 13, 2018, 6 pages.

\* cited by examiner

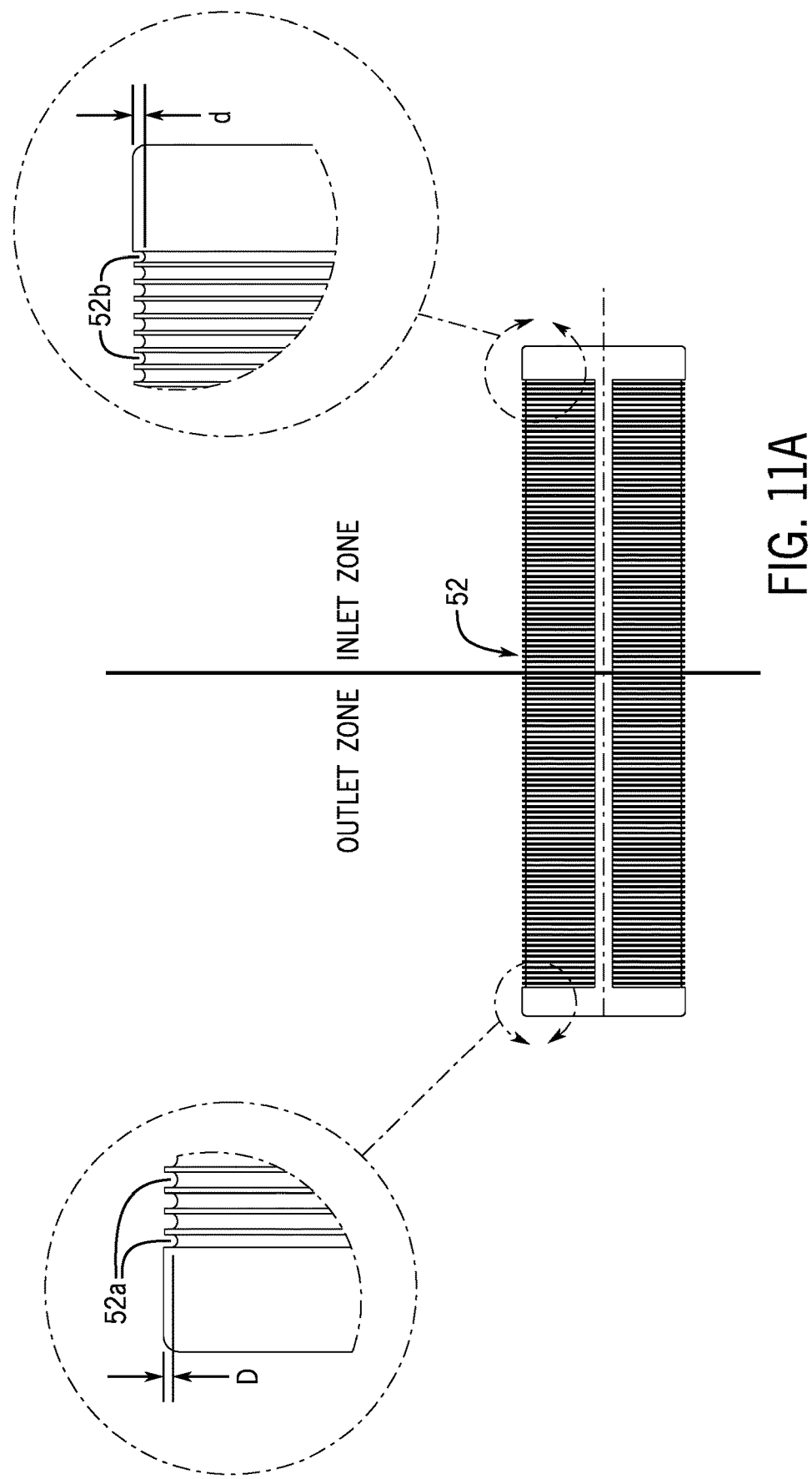

MEMBRANE SEPARATION DEVICE HAVING IMPROVED FILTRATION VELOCITY

CROSS-REFERENCE TO RELATED APPLICATIONS

This application claims the benefit of U.S. Provisional Patent App. No. 62/271,480 filed Dec. 28, 2015, which is expressly incorporated herein by reference in its entirety.

FIELD OF THE DISCLOSURE

The present disclosure is directed to separation devices of the type employing relatively rotating surfaces, at least one of which carries a membrane for filtering a component from fluid passed between the surfaces.

BACKGROUND

Different types of blood collection procedures exist, including manual collection of whole blood from healthy donors through blood drives, donor visits to blood centers or hospitals and the like. In typical manual collection, whole blood is collected by simply flowing it, under the force of gravity and venous pressure, from the vein of the donor into a collection container. The amount of whole blood drawn is typically a "unit" which is about 450 to 550 mL.

Collection may employ a pre-assembled arrangement of tubing and containers or bags, including a flexible plastic primary container or bag for receiving a unit of whole blood from a donor and one or more "satellite" containers or bags. The blood may first be collected in the primary container, which also contains an anticoagulant (typically containing sodium citrate, phosphate and dextrose—often referred to as CPD). A preservative (often called an "additive solution" or AS, and commonly containing a saline, adenine and glucose medium-which is referred to as SAG) may be included as part of a larger assembly of containers and tubes that are used in processing after the blood is collected.

After collection of a unit of whole blood, the unit of whole blood, with connected tubing and containers, may be transported to a blood component processing laboratory, commonly referred to as a "back lab," for further processing. Further processing may entail loading the primary container and associated tubing and satellite containers into a centrifuge to separate the whole blood into components such as concentrated red cells and platelet-rich or platelet-poor plasma. These components are then manually expressed from the primary container into other pre-connected satellite containers, and may again be centrifuged to separate the platelets from plasma. Subsequently, the blood components may be leukoreduced by filtration for further processing or storage. The process may be time-consuming, labor intensive, and subject to possible human error.

Blood banks and transfusion centers may also perform the task of "cell washing," which removes and/or replaces the liquid medium (or a part thereof) in which the cells are suspended, to concentrate or further concentrate cells in a liquid medium, and/or to purify a cell suspension by the removal of unwanted cellular or other material.

Cell washing systems may involve centrifugation of a cell-suspension, decanting of the supernatant, re-suspension of concentrated cells in new media, and possible repetition of these steps until the cells of the suspension are provided at an adequately high or otherwise desirable concentration. Centrifugal separators used in the processing of blood and blood components may be used in such cell-washing methods.

Blood separation apparatus and procedures may employ a separation membrane to separate blood components instead of a centrifuge. This type of device includes relatively rotating surfaces, at least one or which carries a porous membrane. The device may have an outer stationary housing and an internal spinning rotor covered by a porous membrane.

SUMMARY

According to an exemplary embodiment, the present disclosure is directed to a blood filtration device comprising a generally cylindrical housing having an interior wall. An interior member is mounted interior of the housing and comprises an outer surface having a porous membrane disposed thereon. The housing and interior ember are relatively rotatable and define an annular gap therebetween. The blood filtration device also comprises an inlet for directing fluid into the annular gap, a first outlet for exiting filtrate passing through the membrane, and a second outlet for directing from the annular gap the remaining retentate. The porous membrane comprises a first layer and a second layer.

According to an exemplary embodiment, the present disclosure is directed to a blood filtration device comprising a generally cylindrical housing having an interior wall. An interior member is mounted interior of the housing and comprises an outer surface having a porous membrane disposed thereon, wherein the outer surface comprises a plurality of circumferential grooves having two or more depth values. The housing and interior member are relatively rotatable and define an annular gap between the housing and outer surface of the interior member. The blood filtration device comprises an inlet for directing fluid into the annular gap, a first outlet for exiting filtrate passing through the membrane, and a second outlet for directing from the annular gap the remaining retentate. The porous membrane comprises a first layer and a second layer.

According to an exemplary embodiment, the present disclosure is directed to a blood filtration device comprising a generally cylindrical housing having an interior wall. An interior member is mounted interior of the housing and comprises an outer surface having a porous membrane disposed thereon, wherein the outer surface comprises a plurality of circumferential grooves having two or more depth values. The blood filtration device comprises an opening disposed at an end of the outer surface leading to an interior of the interior member. A plurality of longitudinal grooves interconnect the circumferential grooves, and the housing and interior member are relatively rotatable and define an annular gap therebetween. The device comprises an inlet for directing fluid into the annular gap, a first outlet in communication with the interior of the interior member for releasing filtrate passing through the membrane, and a second outlet for directing from the annular gap the remaining retentate. The porous membrane comprises a first layer and a second layer.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

FIG. 11A is a side view of the internal member with expanded views of the circumferential grooves at two different zones, according to an exemplary embodiment.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may increase the efficiency of separation devices, systems, and methods applicable to blood collection and processing.

A description of a spinning membrane separator may be found in U.S. Pat. No. 5,194,145 to Schoendorfer, which is incorporated by reference herein in its entirety, and describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection container. The remaining blood components, primarily red blood cells, platelets and white cells, move to the exit region between the spinner and the shell and may be returned to the donor or collected for further processing.

Spinning membrane separators may provide excellent filtration rates, due primarily to the unique flow patterns ("Taylor vortices") induced in the gap between the spinning membrane and the shell. The Taylor vortices help to keep the blood cells from depositing on and fouling or clogging the membrane.

Other examples of spinning membrane separators are described in U.S. Pat. No. 5,053,121 and U.S. Pat. Pub. No. 2014/0010738, both of which are incorporated by reference herein in their entireties.

Figure 1:
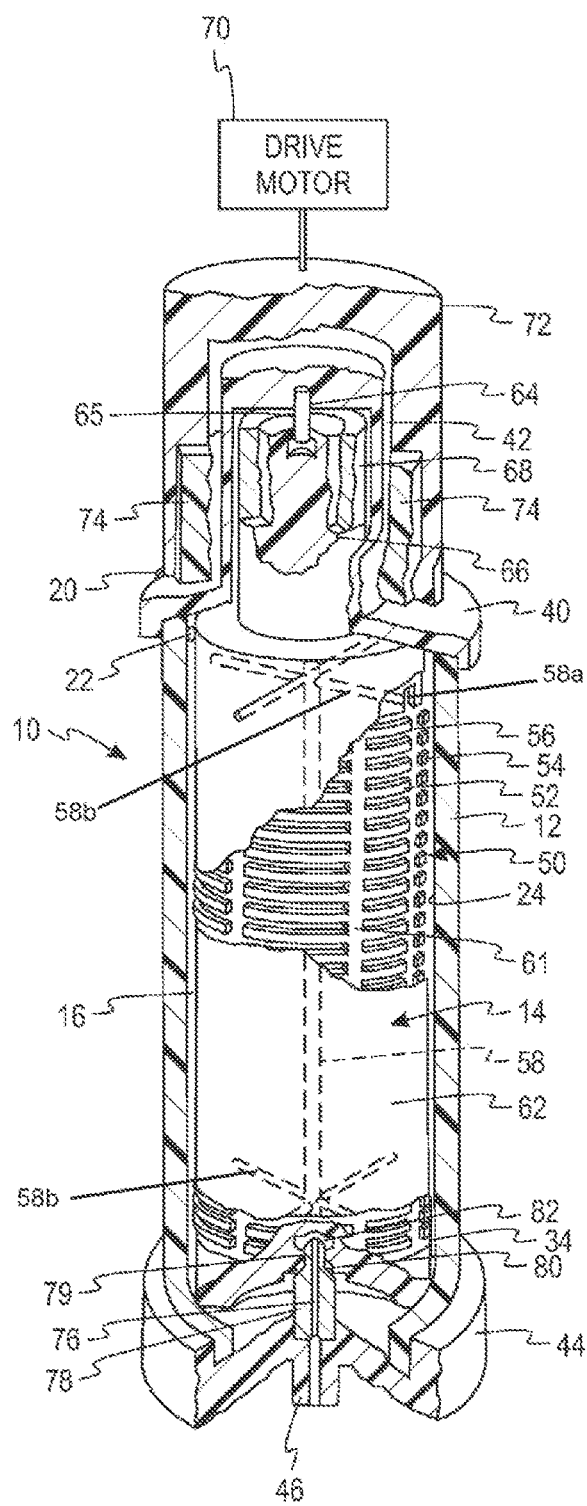
FIG. 1 is a perspective view of a spinning membrane separator, in partial cross section and with portions removed to show detail, according to an exemplary embodiment.
Figure 2:
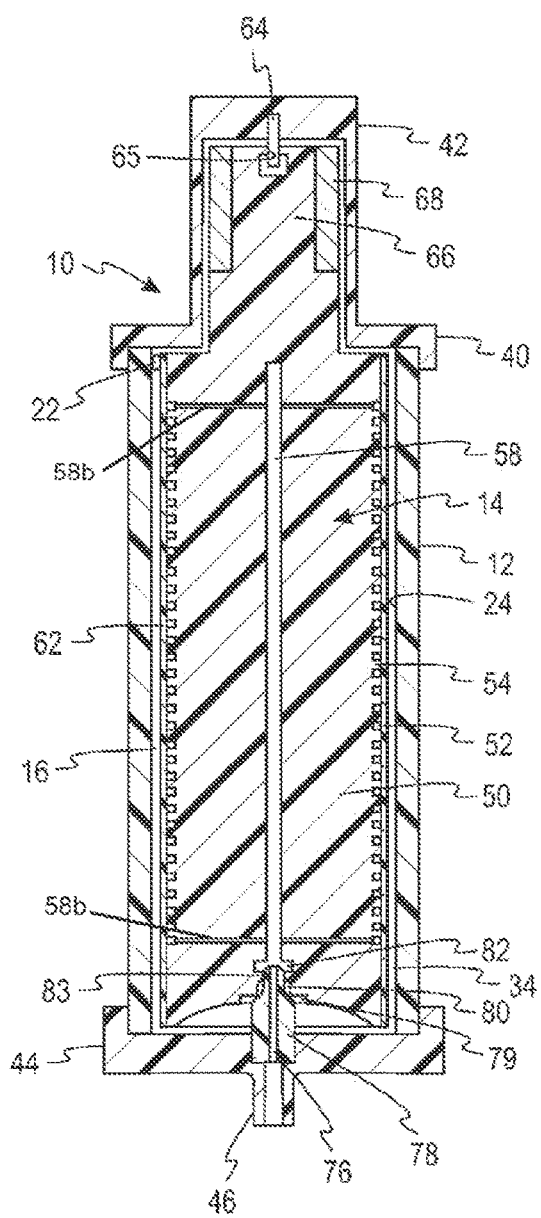
FIG. 2 is a longitudinal cross sectional view of the spinning membrane separator of FIG. 1, according to an exemplary embodiment.

Turning to FIGS. 1 and 2, a spinning membrane blood separation or fractionation system, generally designated 10, is shown. Such a system 10 may be used to extract plasma and red blood cells from whole blood obtained from a donor. Only the separation device and the associated drive unit are shown, but it should be understood that such a separator may be part of a disposable system including collection containers, containers of additives such as saline, SAG, or ACD, return containers, tubing, etc., and that there are also associated control and instrumentation systems for operation of the device.

The system 10 may include a generally cylindrical housing 12, mounted concentrically about a longitudinal vertical central axis. An internal member 14 may be mounted concentric with the central axis. The housing and internal member are relatively rotatable. The housing 12 may be stationary and the internal member 14 may be a rotating spinner that is rotatable concentrically within the cylindrical housing 12. The boundaries of the blood flow path may generally be defined by the gap 16 between the interior urface of the housing 12 and the exterior surface of the rotary spinner 14. The spacing between the housing 12 and the spinner 14 can be referred to as the shear gap. A typical shear gap may be approximately 0.025-0.050 inches (0.067-0.127 cm) and may be of a uniform dimension along the axis, for example, where the axis of the spinner and housing are coincident. The shear gap may also vary circumferentially for example, where the axis of the housing and spinner are offset.

The shear gap 16 may vary along the axial direction. For example, an increasing gap width in the direction of flow may be implemented to limit hemolysis. Such a gap width may range from about 0.025 to about 0.075 inches (0.06-0.19 cm). For example, the axes of the housing 12 and rotor 14 could be coincident and the diameter of the rotor 14 decrease in the axial direction (direction of flow) while the diameter of inner surface of the housing 12 remains constant or the diameter of the housing 12 increases while the rotor 14 diameter remains constant, or both surfaces vary in diameter. The gap width may be varied by varying the outer diameter of the rotor 14 and/or the inner diameter of the facing housing surface. The width dimension of the gap 16 may be selected so that at the desired relative rotational speed, Taylor-Couette flow, such as Taylor vortices, are created in the gap and hemolysis is limited.

Referring to FIGS. 1 and 2, whole blood may be fed from an inlet conduit 20 through an inlet orifice 22, which directs the blood into the blood flow entrance region in a path tangential to the circumference about the upper end of the spinner 14. At the bottom end of the cylindrical housing 12, the housing inner wall includes an exit orifice 34. The cylindrical housing 12 may be completed by an upper end cap 40 and a bottom end housing 44 terminating in a plasma outlet orifice 46 concentric with the central axis.

The spinner 14 may be rotatably mounted between the upper end cap 40 and the bottom end housing 44. The spinner 14 may comprise a shaped central mandrel or rotor 50, the outer surface of which may be shaped to define a series of spaced-apart circumferential grooves or ribs 52 separated by annular lands 54. The surface channels defined by the circumferential grooves 52 may be interconnected by longitudinal grooves 56. At one or more ends of the mandrel 50, these grooves 56 may be in communication with a central orifice or manifold 58 via an opening 58a and bridge 58b.

The surface of the rotary spinner 14 may be at least partially or entirely covered by a cylindrical porous membrane 62. The membrane 62 may have a nominal pore size of 0.6 microns, although other pore sizes may alternatively be used. In one embodiment, pore sizes in the range of 0.2 microns to 5 microns may be used. "Pore size" generally refers to the cross-sectional dimension of the pore 24, and not the depth of the pore 24 through the filter layer. For both pores of circular and non-circular shapes, "pore size" generally refers to the smallest cross-sectional dimension of the pores, unless otherwise stated. The membrane 62 may be a fibrous mesh membrane, cast membrane, track-etched membrane, etc. For example, the membrane 62 may have a polyester mesh (substrate) with nylon particles solidified thereon, thereby creating a tortuous path through which only certain sized components will pass. In another embodiment, the membrane may be made of a thin (e.g., approximately 15 micron thick) sheet of, for example, polycarbonate, nylon, and/or both, and pores may be, e.g., approximately 3-5 microns. The pores may be sized to allow small formed components (e.g., platelets, microparticles, etc.) to pass, while the desired cells (e.g., red and/or white blood cells) are collected. In another embodiment, the membrane thickness may be in the range of 10 to 190 microns and have any suitable pore size from 0.2 microns to 5 microns.

The rotary spinner 14 may be mounted in the upper end cap 40 to rotate about a pin 64, which may be press fit into the end cap 40 on one side and seated within a cylindrical bearing surface 65 in an end cylinder 66 forming part of the rotary spinner 14. The internal spinner 14 or outer housing 12 may be rotated by any suitable rotary drive device or system. The end cylinder 66 may be partially encompassed by a ring 68 of magnetic material utilized in indirect driving of the spinner 14. A drive motor 70 exterior to the housing 12 may be coupled to turn an annular magnetic drive member 72 that includes at least a pair of interior permanent magnets 74. As the annular drive member 72 is rotated, magnetic attraction between the ring 68 interior to the housing 12 and the magnets 74 exterior to the housing may lock the spinner 14 to the exterior drive, causing the spinner 14 to rotate.

At the lower end of the rotary spinner 14, the central outlet orifice 58 may communicate with a central bore 76 in an end bearing 78 that is concentric with the central axis. An end bearing seat may be defined by an internal shoulder 80 that forms a lower edge of a central opening 82, which communicates with the plasma outlet orifice 46.

Figure 3:
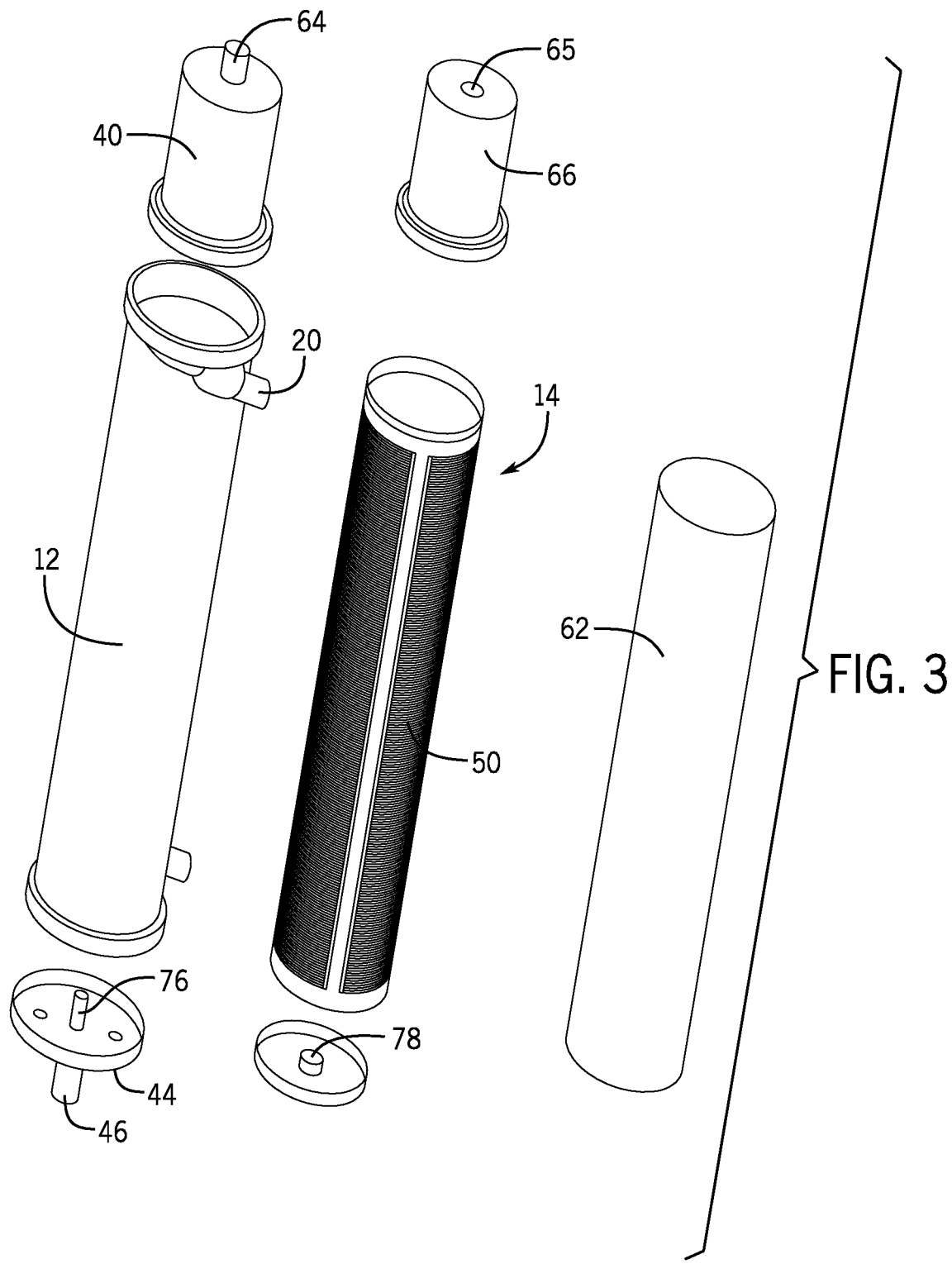
FIG. 3 is an exploded view of the spinning membrane separator of FIGS. 1 and 2, according to an exemplary embodiment.

FIG. 3 is an exploded view of the spinning membrane blood separation or fractionation system 10. As described above, the cylindrical housing 12 of the system 10 may house the internal member 14 concentrically and relatively rotatably about a common central axis. A membrane 62 may cover the internal member 14, and the shear gap 16 may be formed by the spacing between the housing 12 and the spinner 14, with the membrane 62 separating the different blood components.

Optimal filtration leading to successful blood separation procedures may be dependent on several factors. One factor is the membrane filtration velocity, which is the volume of filtrate filtered per unit of time per area of membrane. If volume is measured in $cm^3$, time is measured in minutes, and area of membrane is measured in $cm^2$, the filtration rate may be measured in cm/min. Obtaining higher filtration rates while minimizing hemolysis may enhance separation efficiency and predictability.

Figure 4:
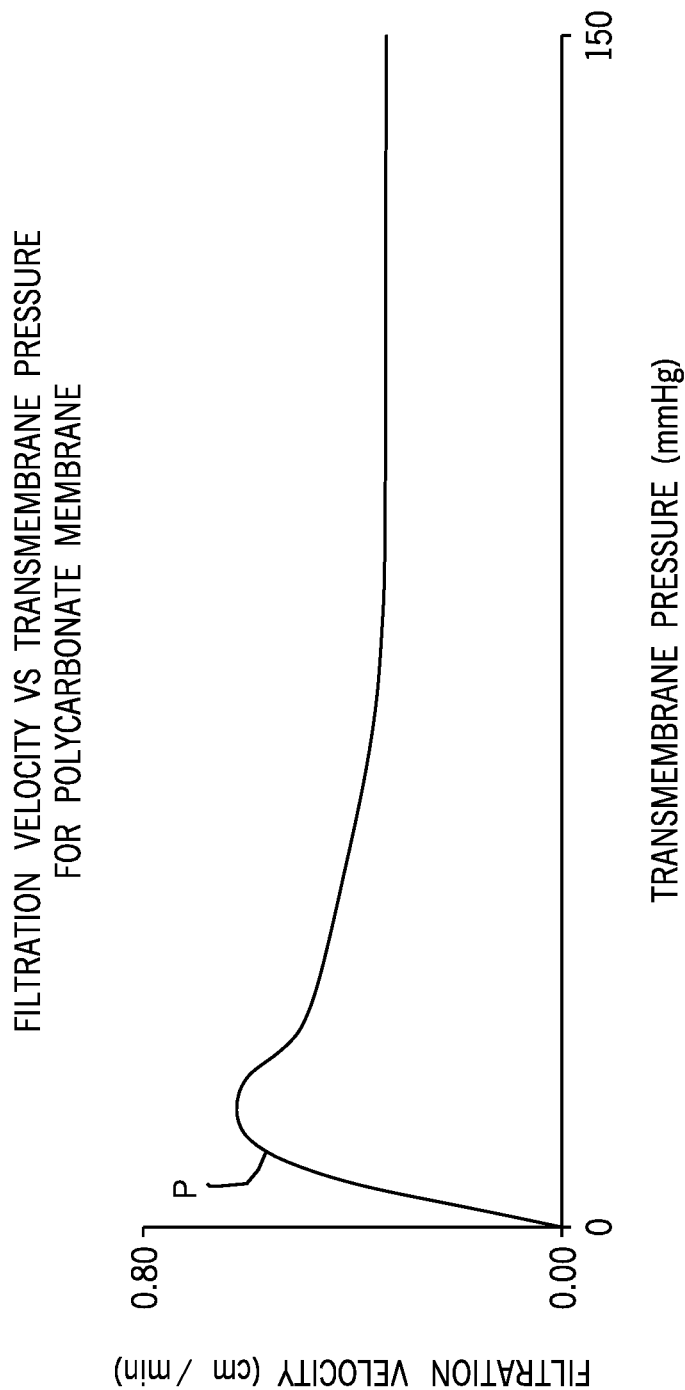
FIG. 4 is a graphical depiction of the general relationship between filtration velocity and transmembrane pressure for a polycarbonate membrane, according to an exemplary embodiment.

A factor that influences filtration rate is transmembrane pressure, which is the pressure differential that exists between the outside and inside of the membrane. To an extent, higher transmembrane pressure may lead to higher filtration rates. FIG. 4 is a graphical depiction of the general relationship between filtration velocity and transmembrane pressure for a polycarbonate membrane. The curve of FIG. 4 shows that in general for polycarbonate membranes, filtration velocity increases proportionally with transmembrane pressure until a critical pressure P is reached beyond which filtration velocity no longer increases proportionally with transmembrane pressure. A further increase of transmembrane pressure beyond critical pressure P eventually leads to a decay of filtration velocity. However, for nylon membranes, after reaching a critical pressure point, filtration velocity does not decay but rather gradually continues with a positive slope until reaching an asymptote.

Filtration velocity decreasing despite an increasing transmembrane pressure may be reflective of an obstruction of flow. The polycarbonate membrane may collapse against the internal member 14, especially as fluid outside the membrane 62 becomes denser towards orifices 34 and 46 as the plasma concentration outside the membrane decreases due to having crossed the membrane 62.

Figure 5:
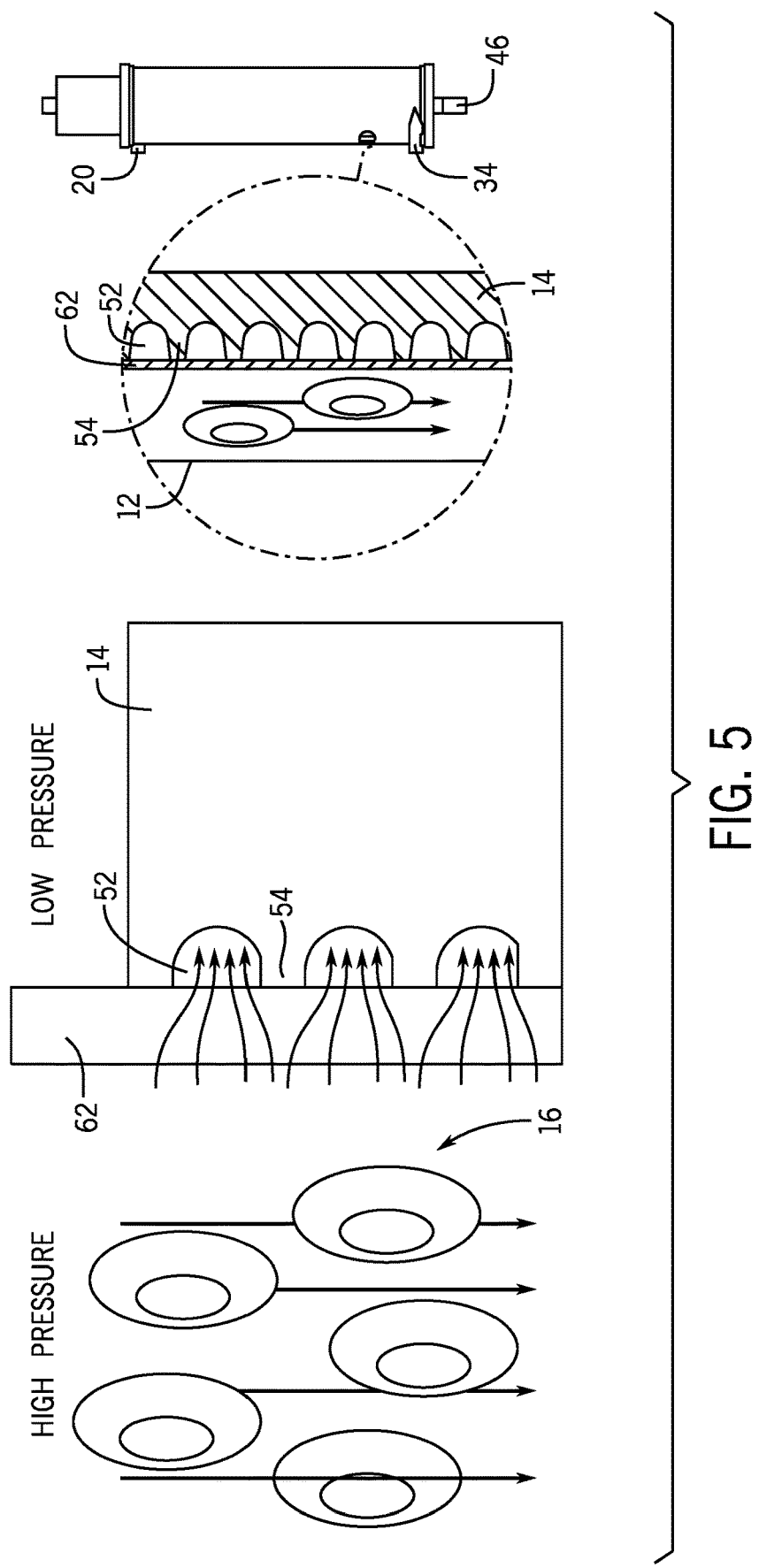
FIG. 5 is an expanded view of a portion of the spinning membrane separator, showing the interaction between the membrane and grooves of the internal member, according to an exemplary embodiment.

FIG. 5 is a pictorial depiction of the interaction between the membrane 62 and the grooves 52 of the internal member 14. As fluid moves downwards within the gap 16 between the housing 12 and the internal member 14, the plasma continuously crosses the membrane 62 into the grooves 52 of the internal member 14. The density outside the membrane 62 towards the orifices 34 and 46 increases and exerts increasing pressure on the membrane 62. The increasing pressure on membrane 62 may result in restricted flow within the grooves 52 of the internal member 14 due to collapsing of the polycarbonate membrane against a portion of a groove 52. Restricted flow within the grooves 52 may in turn result in restricted flow across the membrane 62 as well as restricted axial/longitudinal flow (FIG. 9) towards opening 58a that leads to the plasma bridge 58b (FIG. 1).

Figure 6:
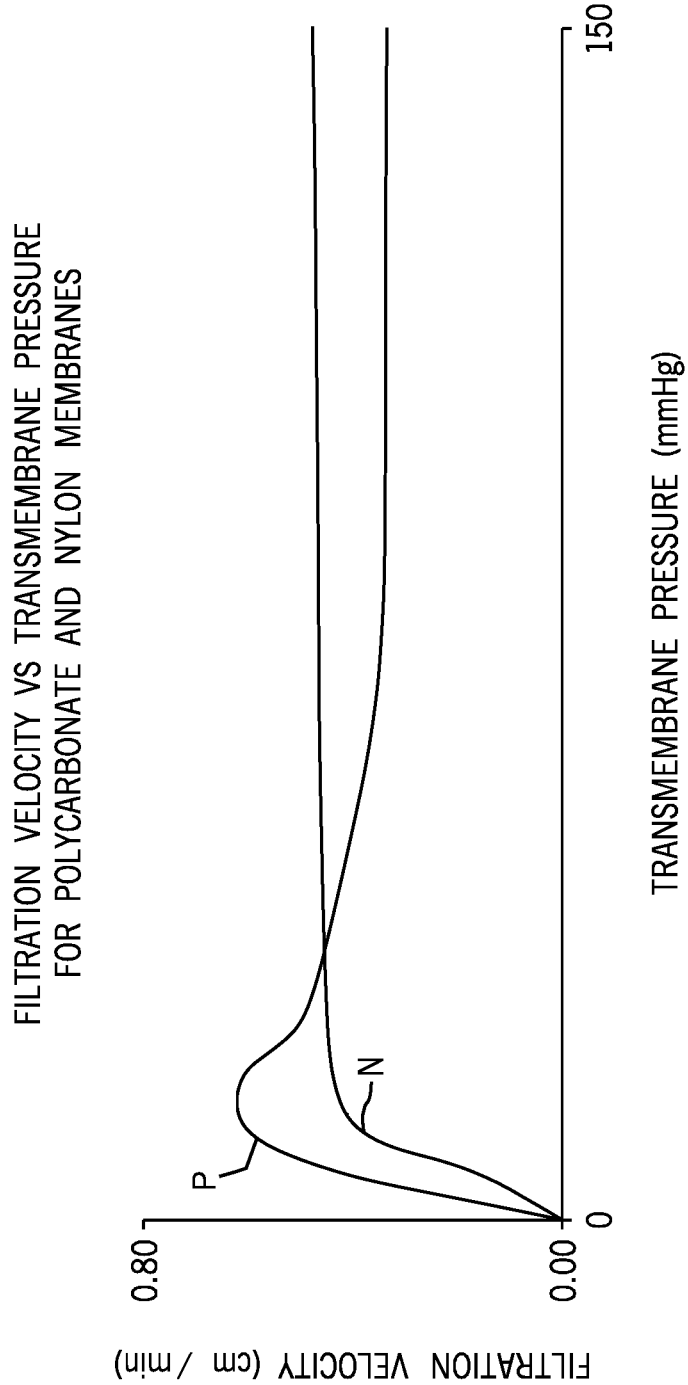
FIG. 6 is a graphical depiction of the general relationship between filtration velocity and transmembrane pressure for a nylon membrane and a polycarbonate membrane, according to an exemplary embodiment.

FIG. 6 is a graphical depiction of the general relationship between filtration velocity and transmembrane pressure for a nylon membrane as well as a polycarbonate membrane. Compared to the polycarbonate membrane curve, the nylon membrane curve, after reaching its critical pressure point N at which the curve is no longer linear, does not decay but rather gradually continues with a positive slope until reaching an asymptote. However, the nylon membrane curve does not reach a peak level as high as that reached by the polycarbonate membrane.

Figure 7:
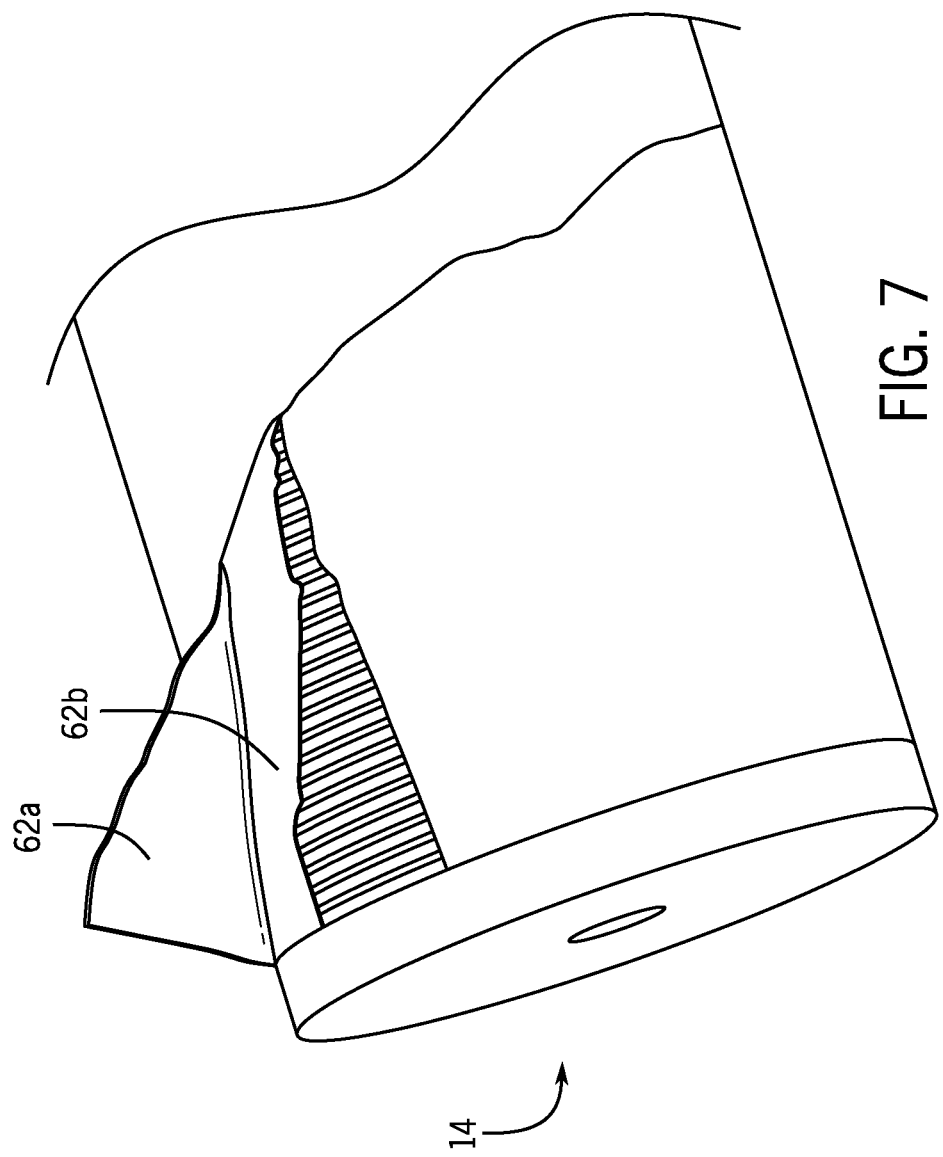
FIG. 7 is a perspective view of one end of the internal rotor of the spinning membrane separator, according to an exemplary embodiment.
Figure 8:
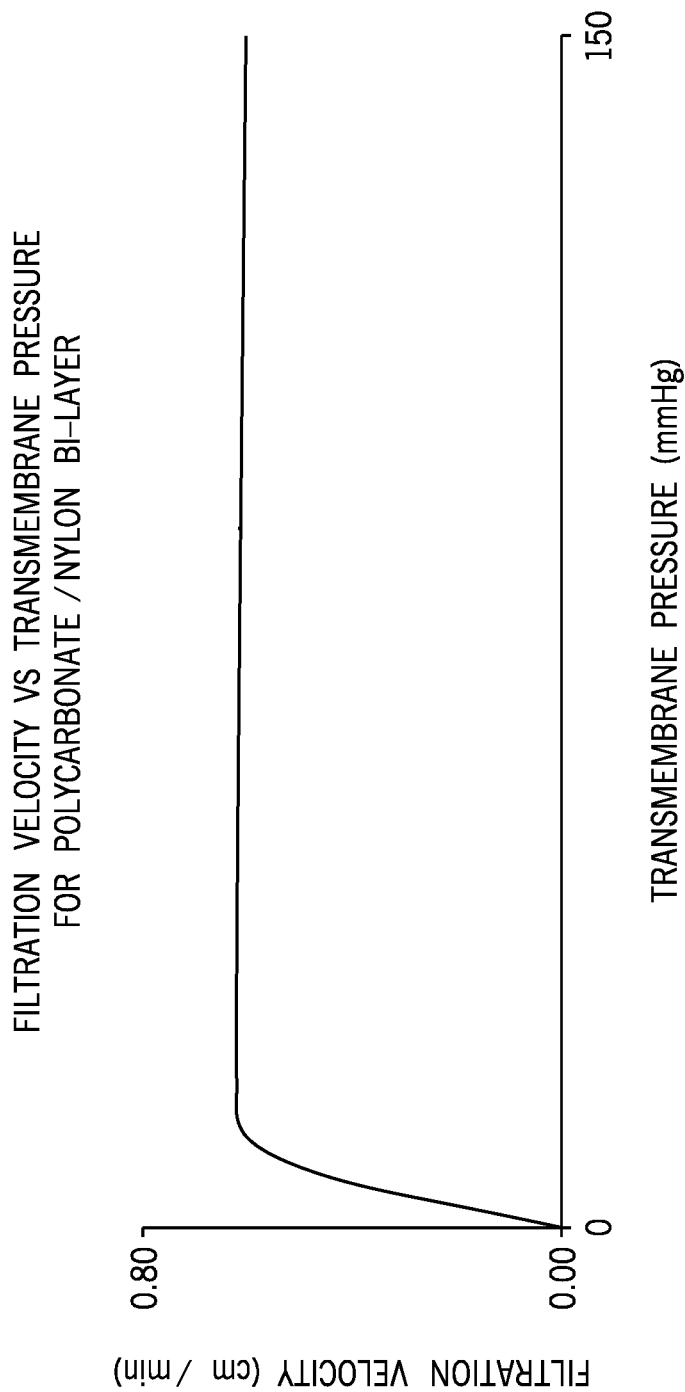
FIG. 8 is a graphical depiction of the general relationship between filtration velocity and transmembrane pressure for a multi-layer membrane, according to an exemplary embodiment.

FIG. 7 depicts one end of the internal rotor 14 with a membrane 62 comprising two layers. The two layers may include a polycarbonate layer 62a and a nylon layer 62b. In one embodiment, the nylon layer 62b may be disposed underneath the polycarbonate layer 62a and act as a scaffold/support for the polycarbonate layer 62a to prevent collapse of the polycarbonate membrane 62a into the grooves. The nylon layer 62b should have a thickness value and an air permeability value that is conducive to the nylon layer's ability to support the polycarbonate layer 62a while minimizing obstruction or hindrance of fluid flow. In one embodiment, the nylon layer 62b may have a thickness of 40-80 microns and an air permeability of 50-130 cc/cm^2/sec, FIG. 8 is a graphical depiction of the general relationship between filtration velocity and transmembrane pressure that results from a multi-layer membrane comprising a polycarbonate layer 62a and a nylon layer 62b. As shown in FIG. 8, the filtration velocity reaches a level similar to the peak level exhibited by a polycarbonate membrane alone and also maintains a positive slope until reaching an asymptote, as exhibited by a nylon membrane. The nylon layer 62a acting as a support helps minimize or eliminate the decay due to membrane collapse exhibited by a polycarbonate membrane curve and thereby sustain peak levels even as transmembrane pressure increases.

The scaffold/support layer may comprise nylon in one embodiment, but in an alternate embodiment, the scaffold/support layer may comprise another suitable material or combination of materials. For example, in one embodiment, the scaffold/support layer may comprise polyester and/or a polyester blend. The outer layer may comprise a polycarbonate layer in one embodiment, but in an alternate embodiment, the outer layer may comprise another suitable material or combination of materials. For example, polyethersulfone (PES) and/or a PES blend may be used as an outer layer in one embodiment.

Figure 9:
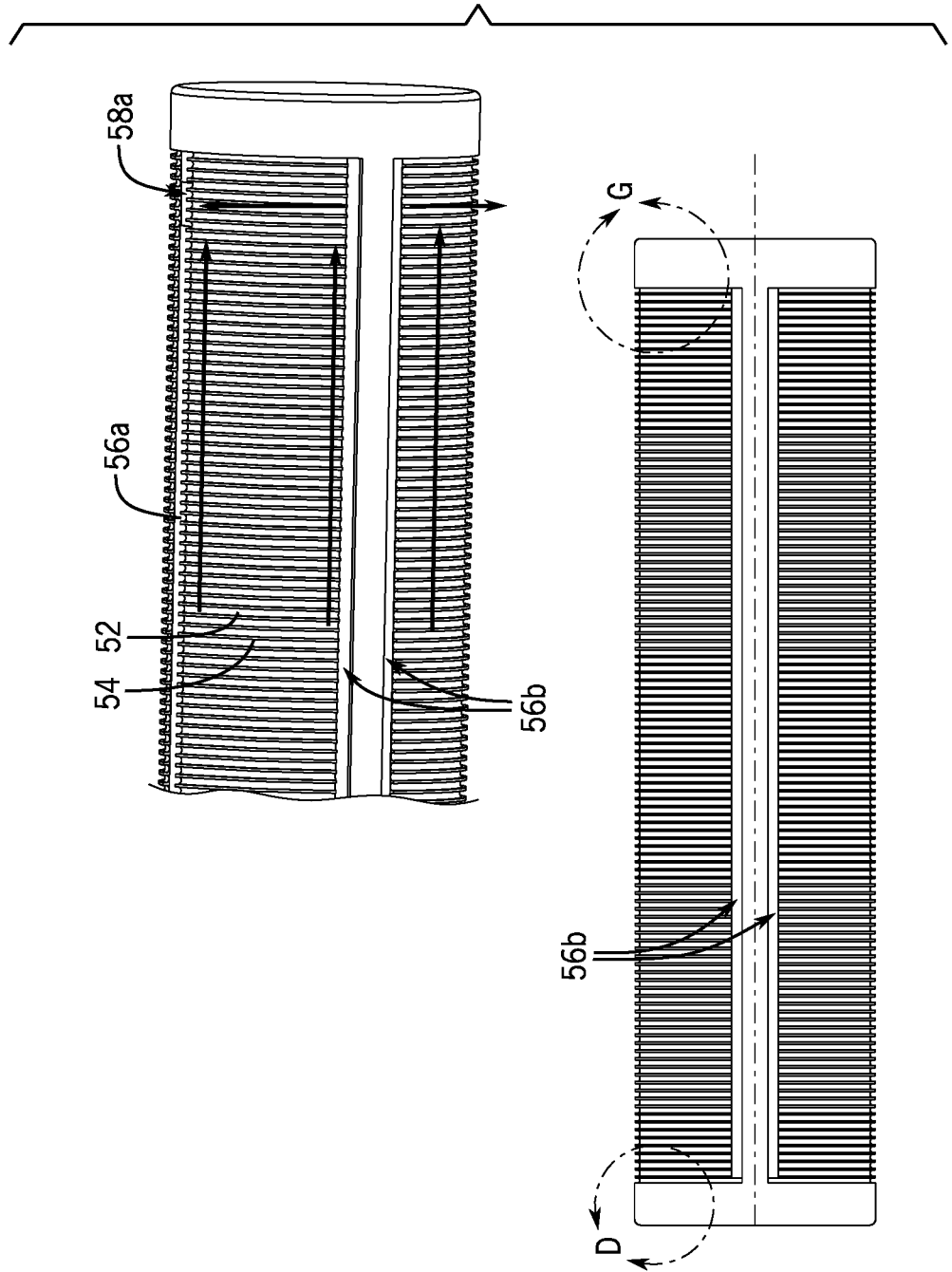
FIG. 9 is a perspective side view of the internal rotor showing different flow paths, according to an exemplary embodiment.

Turning to FIG. 9, a perspective side view of the internal rotor 14 is shown. Opening 58a that leads to plasma bridge 58b (FIG. 1) is disposed near an end of the internal rotor proximal to outlet orifices 34 and 46. Grooves 52 separated by annular lands 54 may be disposed circumferentially and serially along the length of the internal member 14. Longitudinal groove 56a may run along the length of internal member 14 and be proximal to or coincide with plasma opening 58a leading to the plasma bridge 58b. Longitudinal groove 56a may also interconnect the circumferential grooves 52. Internal member 14 may have a second longitudinal groove 56b that also runs along the length of internal member 14 and interconnects the circumferential grooves 52 but is distal from or does not coincide with plasma opening 58a. Longitudinal groove 56b may provide a second collection pathway by which plasma flow can be directed towards the plasma bridge 58b through opening 58a.

Figure 10:
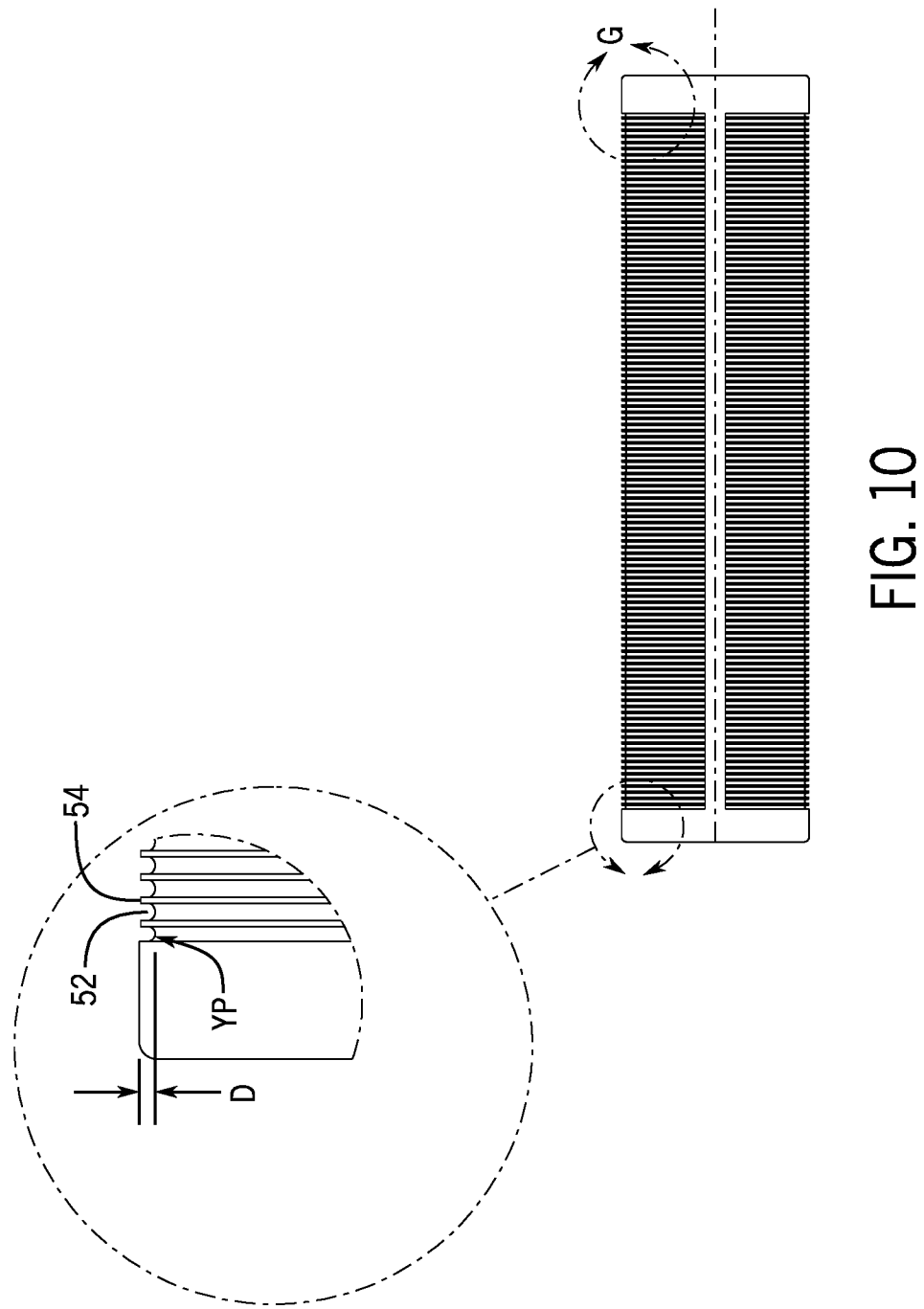
FIG. 10 is a side view of the internal member with an expanded view of the circumferential grooves, according to an exemplary embodiment.

Turning to FIG. 10, a side view of the internal member 14 with an expanded view of the circumferential grooves 52 is shown. The nylon layer 62b of FIG. 7 providing a support for polycarbonate layer 62a and minimizing potential collapse of the membrane 62 against a portion of groove 52 may allow for deeper grooves 52 than would a polycarbonate layer alone. When using a polycarbonate layer 62a alone, the practicable depth value of grooves 52 may be limited due to a positive relationship between depth value and difficulty of membrane collapse reversal, given that a membrane having collapsed deeper within a groove would be less likely to return to its un-collapsed position.

With a nylon-polycarbonate multi-layer being more resistant to collapse and allowing for deeper grooves, the deeper grooves may be conducive to accommodating higher volume of fluid collection by the internal rotor 14 as higher filtration velocity is sustained. Groove depth D in FIG. 10 is the distance between the top edge of the annular land 54 and the bottom of groove 52. In one embodiment, depth D may be greater than 0.033 inches and preferably approximately 0.066 inches up to 0.099 inches. In addition to deeper grooves being able to accommodate higher volume of fluid collection by the internal rotor 14, a greater depth D may allow for minimal hindrance of the collection process in the event that some collapse of the membrane 62 against a portion of groove 52 occurs.

FIG. 11A depicts a side view of the internal member 14 with an expanded view of the circumferential grooves 52 proximal to outlet orifices 34 and 46 and an expanded view of the circumferential grooves 52 proximal to inlet conduit 20. As fluid outside the membrane 62 becomes denser towards orifices 34 and 46 as the plasma concentration outside the membrane decreases, the likelihood of collapse of the membrane 62 against a portion of a groove 52 may increase. In such an event, deeper grooves 52 may allow for continuous flow of filtrate through grooves 52 even though a top portion of space of the groove 52 is taken up by material of the membrane 62.

Turning to FIG. 11A, in one embodiment, circumferential grooves 52a proximal to outlet orifices 34 and 46 may each have depth D approximately 0.066 inches up to 0.099 inches, and circumferential grooves 52b proximal to inlet conduit 20 may each have depth d approximately 0.033 to 0.066 inches. Grooves 52b proximal to inlet conduit 20 may be shallower than grooves 52a proximal to orifices 34 and 46, as the density of fluid surrounding grooves 52b proximal to inlet conduit 20 may be lower than that of grooves 52a proximal to orifices 34 and 46.

Figure 11B:
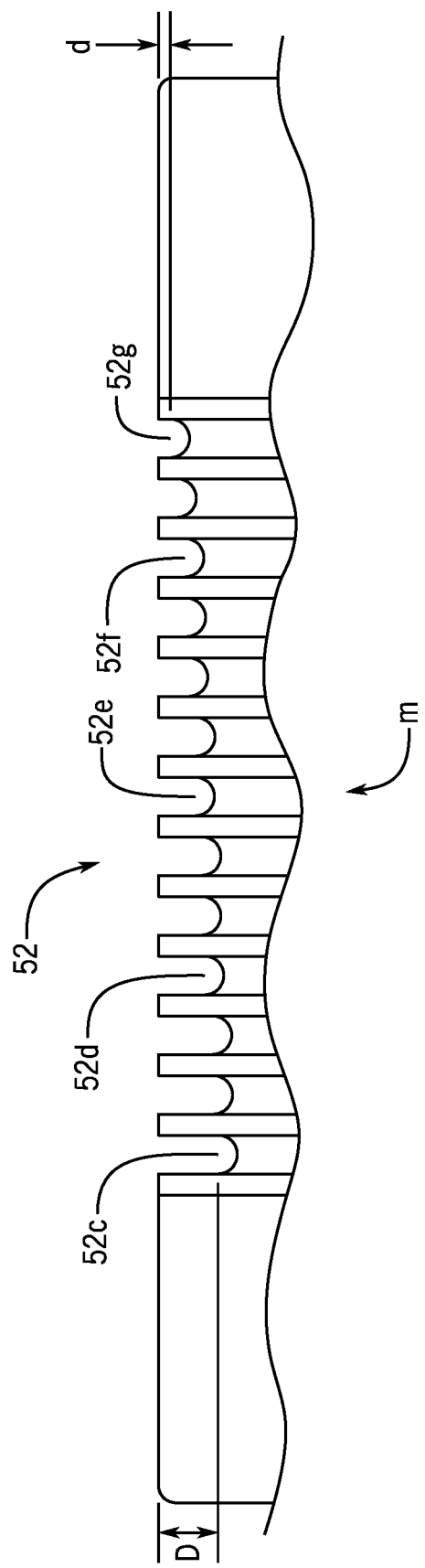
FIG. 11B is a side view of the internal member with an expanded view of the circumferential grooves at a portion along the length of the internal member, according to an exemplary embodiment.

In an alternate embodiment as depicted in FIG. 11B, grooves 52 may gradually increase longitudinally in depth D along the length of internal member 14 from the end proximal to inlet conduit 20 to the end proximal to orifices 34 and 46. In this embodiment, depth D may be as low as 0.033 inches at the end proximal to inlet conduit 20, incrementally increase to approximately 0.066 inches at a point m at any point between the end proximal to inlet conduit 20 and the end proximal to orifices 34 and 46, and incrementally increase up to 0.099 inches at the end proximal to outlet orifices 34 and 46. For example, in FIG. 11B, a groove 52c most proximal to orifices 34 and 46 may have depth D of 0.087 to 0.099 inches, while a groove 52g most proximal to the inlet conduit 20 may have depth d of 0.033 to 0.048 inches. A groove 52e proximal to point m may have depth D of approximately 0.066 inches and preferably in the range of 0.054 to 0.078 inches. A groove 52d located between groove 52c and 52e may have depth D of approximately 0.083 inches or any value from depth D of groove 52c to depth D of groove 52e. In one embodiment, groove 52d may have depth D in the range of 0.070 to 0.095 inches. A groove 52f located between groove 52e and 52g may have depth d of approximately 0.050 inches or any value from depth d of groove 52g to depth D of groove 52e. In one embodiment, groove 52f may have depth d in the range of 0.038 to 0.062 inches.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A blood filtration device for separating blood into two or more components, comprising:
   an outer housing having an interior wall;
   an internal member mounted interior of the outer housing comprising a rotor having an outer surface defining a circumference with a cylindrical porous membrane disposed thereon for separation of blood into a filtrate that passes through the membrane and a retentate that does not pass through the membrane, wherein the outer surface of the rotor comprises a plurality of-discrete circumferential grooves, including a first circumferential groove and a second circumferential groove, each discrete circumferential groove being defined by a pair of annular lands having a top edge and a bottom and having a uniform depth about the circumference of the rotor, the depth of each discrete circumferential groove being defined as a distance between the top edges of the annular lands and the bottom defining the discrete groove, at least the first circumferential groove having a uniform depth different from the uniform depth of the second circumferential groove;

the outer housing and internal member being relatively rotatable and defining an annular gap between the outer housing and outer surface of the internal member;

an inlet for directing fluid into the annular gap;

a first outlet for exiting filtrate passing through the porous membrane; and second outlet for directing from the annular gap retentate remaining in the annular gap;

wherein the porous membrane comprises afirst layer and a second layer, the second layer being supported on the first layer.

2. The device of claim 1, wherein the first and/or second layer comprises at least one of a fibrous mesh membrane, cast membrane, and track-etched membrane.

3. The device of claim 1, wherein the fluid comprises whole blood, the filtrate comprises plasma and/or platelets, and the retentate comprises blood cells.

4. The device of claim 1, wherein a first axial portion of the outer surface comprises circumferential grooves having a first groove depth, and a second axial portion of the outer surface comprises circumferential grooves having a second groove depth different from the first groove depth.

5. The device of claim 1, wherein the circumferential grooves have incrementally increasing groove depths along a length of the outer surface from 0.033 inches to 0.099 inches.

6. The device of claim 5, wherein the increasing groove depths proceed in a direction from a first end of the internal member proximal to the inlet to a second end of the internal member proximal to the first outlet and/or the second outlet.

7. The device of claim 1, wherein the first layer of the porous membrane is an inner layer comprising nylon or polyester and the second layer of the porous membrane is an outer layer comprising polycarbonate or polyethersulfone.

8. The device of claim 1, wherein at least one of the first and second layers of the porous membrane comprises pores having sizes in the range of 0.2 microns to 5 microns, and at least one of the first and second layers comprises a thickness of 40 to 80 microns and an air permeability of 50 to 130 cc/cm$^2$/sec.

9. A blood filtration device for separating blood into two or more components, comprising:

an outer housing having an interior wall;

an internal member mounted interior of the outer housing comprising a rotor having an outer surface defining a circumference with a cylindrical porous membrane disposed thereon for separation of blood into a filtrate that passes through the membrane and a retentate that does not pass through the membrane, wherein the outer surface of the rotor comprises a plurality of discrete circumferential grooves, including a first circumferential groove and a second circumferential groove, each discrete circumferential groove being defined by a pair of annular lands having a top edge and a bottom and having a uniform depth about the circumference of the rotor, the depth of each discrete groove being defined as a distance between the top edges of the annular lands and the bottom defining the discrete groove, at least the first circumferential groove having a uniform depth different from the uniform depth of the second circumferential groove;

an opening disposed at an end of the outer surface leading to an interior of the internal member;

a plurality of longitudinal grooves interconnecting the circumferential grooves;

the outer housing and internal member being relatively rotatable and defining an annular gap therebetween;

an inlet for directing fluid into the annular gap;

a first outlet in communication with the interior of the internal member for releasing filtrate passing through the porous membrane; and a second outlet for directing from the annular gap retentate remaining in the annular gap;

wherein the porous membrane comprises a first layer and a second layer, the second layer being supported on the first layer.

10. The device of claim 9, wherein at least three longitudinal grooves interconnect the circumferential grooves, at least one of which coincides with the opening disposed at the end of the outer surface and at least one of which does not coincide with the opening disposed at the end of the outer surface.

11. The device of claim 9, wherein a first axial portion of the outer surface comprises circumferential grooves having a first groove depth, and a second axial portion of the outer surface comprises circumferential grooves having a second groove depth different from the first groove depth.

12. The device of claim 9, wherein the circumferential grooves have incrementally increasing groove depths along a length of the outer surface from 0.033 inches to 0.099 inches.

13. The device of claim 12, wherein the increasing groove depths proceed in a direction from a first end of the internal member proximal to the inlet to a second end of the internal member proximal to the first outlet and/or the second outlet.

14. The device of claim 9, wherein the porous membrane comprises a first layer and a second layer and wherein the first layer is an inner layer comprising nylon or polyester and the second layer is an outer layer comprising polycarbonate or polyethersulfone.

15. The device of claim 9, wherein the porous membrane comprises a first layer and a second layer and wherein at least one of the first layer and second layers comprises pores having sizes in the range of 0.2 microns to 5 microns, and at least one of the first and second layers comprises a thickness of 40 to 80 microns and an air permeability of 50 to 130 cc/cm$^2$/sec.

16. The device of claim 9, wherein the porous membrane comprises a first layer and a second layer and wherein at least one of the first and second layers comprises at least one of a fibrous mesh membrane, cast membrane, and track-etched membrane.

* * * * *